(12) United States Patent
Lei et al.

(10) Patent No.: US 11,325,907 B2
(45) Date of Patent: May 10, 2022

(54) CRYSTAL FORM OF 1H-IMIDAZO[4,5-B]PYRIDINE-2(3H)-ONE COMPOUND AND PREPARATION PROCESS THEREFOR

(71) Applicant: MEDSHINE DISCOVERY INC., Jiangsu (CN)

(72) Inventors: Maoyi Lei, Shanghai (CN); Yu Xu, Shanghai (CN); Yunfu Luo, Shanghai (CN)

(73) Assignee: Medshine Discovery Inc., Jiangsu (CN)

( * ) Notice: Subject to any disclaimer, the term of this patent is extended or adjusted under 35 U.S.C. 154(b) by 0 days.

(21) Appl. No.: 16/965,377

(22) PCT Filed: Jan. 29, 2019

(86) PCT No.: PCT/CN2019/073701
§ 371 (c)(1),
(2) Date: Jul. 28, 2020

(87) PCT Pub. No.: WO2019/144970
PCT Pub. Date: Aug. 1, 2019

(65) Prior Publication Data
US 2021/0198253 A1    Jul. 1, 2021

(30) Foreign Application Priority Data
Jan. 29, 2018  (CN) .......................... 201810085704.1

(51) Int. Cl.
*C07D 471/04* (2006.01)
*A61P 19/02* (2006.01)

(52) U.S. Cl.
CPC ............ *C07D 471/04* (2013.01); *A61P 19/02* (2018.01); *C07B 2200/13* (2013.01)

(58) Field of Classification Search
CPC ........ C07D 471/04; A61P 19/02; A61P 11/00; A61P 1/00; A61P 17/06; A61P 29/00; C07B 2200/13
(Continued)

(56) References Cited

U.S. PATENT DOCUMENTS 10,532,986 B2    1/2020   Luo et al.
10,662,189 B2    5/2020   Luo et al.
(Continued)

FOREIGN PATENT DOCUMENTS

CN    105407888 A    3/2016
WO    2006025991 A2  3/2006
(Continued)

OTHER PUBLICATIONS

International Search Report dated Apr. 28, 2019 in International Application No. PCT/CN2019/073701.
(Continued)

*Primary Examiner* — Taylor V Oh
(74) *Attorney, Agent, or Firm* — Ice Miller LLP

(57) ABSTRACT

Disclosed are a crystal form of 1H-imidazo[4,5-b]pyridine-2(3H)-one compound and a preparation process therefor, and use of the crystal form in the manufacture of a medicament for treating a disease associated with PDE4 receptor.
(Continued)

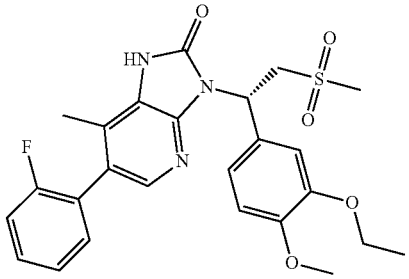

(I)

14 Claims, 2 Drawing Sheets

(58) Field of Classification Search
USPC .................................................. 514/303
See application file for complete search history.

(56) References Cited

U.S. PATENT DOCUMENTS

2011/0319394 A1  12/2011  Taniguchi
2012/0178708 A1  7/2012  Kumar

FOREIGN PATENT DOCUMENTS

| WO | 2011021678 A1 | 2/2011 |
| WO | 2015002754 A2 | 1/2015 |
| WO | 2015175956 A1 | 11/2015 |
| WO | 2018036469 A1 | 3/2018 |
| WO | 2018036470 A1 | 3/2018 |

OTHER PUBLICATIONS

Written Opinion dated Apr. 28, 2019 in International Application No. PCT/CN2019/073701.
Jul. 29, 2021 EESR issued in European application No. 19743686.8.
Caira, Mino R.: "Crystalline Polymorphism of Organic Compounds", Topics in Current Chemistry; [Topics in Current Chemistry], Springer, Berlin, DE, vol. 198, Jan. 1998 (Jan. 1998), pp. 163-208, XP008166276, ISSN: 0340-1022, DOI: 10.1007/3-540-69178-2_5 [retrieved on Feb. 26, 1999].
Hilfiker, R., Blatter, F., von Raumer, M.: "Relevance of Solid-state Properties for Pharmaceutical Prodcuts" In: Hilfiker, R: "Polymorphism in the Pharmaceutical Industry", Jan. 2006 (Jan. 2006), Wiley-VCH, XP002528052, ISBN: 978-3-527-31146-0, pp. 1-19.
Nov. 24, 2021 the First Office Action issued in Indian application No. 202017036372.

CRYSTAL FORM OF 1H-IMIDAZO[4,5-B]PYRIDINE-2(3H)-ONE COMPOUND AND PREPARATION PROCESS THEREFOR

CROSS REFERENCE TO RELATED APPLICATION

This application is a Section 371 of International Application No. PCT/CN2019/073701, filed Jan. 29, 2019, which was published in the Chinese language on Aug. 1, 2019, under International Publication No. WO 2019/144970 A1, which claims priority under 35 U.S.C. § 119(b) to Chinese Patent Application No. 201810085704.1, filed on Jan. 29, 2018, the disclosures of which are incorporated herein by reference in their entireties.

TECHNICAL FIELD

Provided are a Crystal Form of 1H-imidazo[4,5-b]pyridine-2(3H)-one compound and preparing process thereof as well as use of the Crystal Form for the manufacture of a medicament for treating a disease associated with PDE4.

BACKGROUND

Tumor necrosis factor (TNFα) is a cytokine released mainly by monocytes and macrophages in response to immune stimulation. TNFα can promote most processes of cell differentiation, recruitment, proliferation and protein degradation. TNFα has protective effect against infectious agents, tumors and tissue damage at a low level. However, over release of TNFα may also cause disease. For example, when administered to mammals or humans, TNFα may cause or aggravate inflammation, fever, cardiovascular influence, bleeding, blood clotting, and acute reactions similar to acute infection and shock. The production of excessive or uncontrolled TNFα in animals or humans often indicates the following diseases: endotoxemia and/or toxic shock syndrome, cachexia, adult respiratory stress syndrome, cancer (such as solid tumors and hematological tumors), heart disease (such as congestive heart failure), viral infection, genetic disease, inflammatory disease, allergic disease or autoimmune disease.

Cancer is a disease with particular destructiveness, and an increase of the level of TNFα in blood indicates the risk of cancer or the metastasis. Generally, cancer cells cannot survive in the circulatory system of a healthy subject, and one of the reasons is that the inner wall of blood vessels acts as barrier to extravasation of the cancer cells. Studies have shown that ELAM-1 on endothelial cells can mediate the adhesion of colon cancer cells to the endothelium treated with cytokines.

Cyclic adenosine monophosphate (cAMP) plays a role in many diseases and disorders. Increase in cAMP concentration in leukocytes during inflammation suppresses the activation of leukocytes, and subsequently releases inflammatory regulatory factors including TNFα and NF-κB. Increased cAMP levels also leads to relaxation of airway smooth muscles.

The main cellular mechanism of cAMP inactivation is due to the destruction of cAMP by a family of isozymes called cyclic nucleotide phosphodiesterases (PDE). It is known that there are 11 members in the PDE family. So far, inhibition of PDE4 enzyme has been proved to be particularly effective in inhibiting the release of inflammatory mediators and relaxing airway smooth muscle, and therefore PDE4 enzyme has become one of the popular drug targets. According to different genetic coding, the PDE-4 family can be divided into 4 subtypes (PDE-4A, B, C, D). Among them, expression of PDE-4A, PDE-4B and PDE-4D in inflammatory cells (such as B cells, T cells and neutrophils) is stronger than that of PDE-4C. Inhibition of PDE4 enzyme leads to an increase in cAMP levels, thereby adjusting the level of TNFα so as to treat diseases.

SUMMARY

In an aspect, provided is a Crystal Form A of Compound 1, wherein the Crystal Form A has an X-ray powder diffraction pattern having characteristic diffraction peaks at the following 2θ angles: 14.10±0.2°. 19.07±0.2°. 21.79±0.2°.

Compound 1

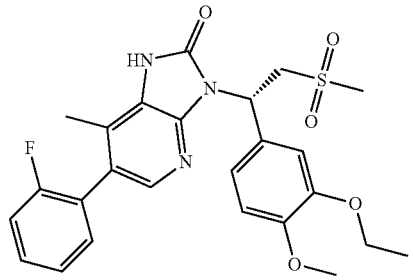

In some embodiments according to the present disclosure, the Crystal Form A of Compound 1 has an X-ray powder diffraction pattern having characteristic diffraction peaks at the following 2θ angles: 10.69±0.2°, 12.31±0.2°, 13.45±0.2°, 14.10±0.2°, 14.62±0.2°, 19.07±0.2°, 20.33±0.2°, 21.79±0.2°.

In some embodiments according to the present disclosure, the Crystal Form A of Compound 1 has an X-ray powder diffraction pattern having characteristic diffraction peaks at the following 2θ angles: 6.25±0.2°, 8.93±0.2°, 10.69±0.2°, 12.31±0.2°, 13.45±0.2°, 14.10±0.2°, 14.62±0.2°, 18.16±0.2°, 19.07±0.2°, 20.33±0.2°, 21.79±0.2°.

In some embodiments according to the present disclosure, the Crystal Form A of Compound 1 has an XRPD pattern as shown in FIG. 1.

In some embodiments according to the present disclosure, the Crystal Form A of Compound 1 has an XRPD pattern with Analysis Data shown in Table 1.

TABLE 1

XRPD Pattern Analysis Data of Crystal Form A of Compound 1

| No. | 2θ angle (°) | Inter-planar spacing (Å) | Relative Intensity (%) |
|---|---|---|---|
| 1 | 6.250 | 14.1293 | 21.2 |
| 2 | 8.932 | 9.8927 | 19.2 |
| 3 | 9.425 | 9.3754 | 9.8 |
| 4 | 10.690 | 8.2687 | 45.3 |
| 5 | 12.306 | 7.1868 | 45.9 |
| 6 | 12.660 | 6.9865 | 29.3 |
| 7 | 13.449 | 6.5783 | 38.0 |
| 8 | 14.098 | 6.2769 | 100.0 |
| 9 | 14.615 | 6.0558 | 28.8 |
| 10 | 15.162 | 5.8386 | 11.5 |
| 11 | 17.417 | 5.0874 | 5.7 |
| 12 | 18.162 | 4.8805 | 24.3 |
| 13 | 18.796 | 4.7173 | 28.0 |

TABLE 1-continued

XRPD Pattern Analysis Data of Crystal Form A of Compound 1

| No. | 2θ angle (°) | Inter-planar spacing (Å) | Relative Intensity (%) |
|---|---|---|---|
| 14 | 19.072 | 4.6496 | 72.4 |
| 15 | 20.333 | 4.3639 | 32.1 |
| 16 | 20.728 | 4.2817 | 27.7 |
| 17 | 21.794 | 4.0746 | 68.2 |
| 18 | 22.739 | 3.9074 | 9.9 |
| 19 | 22.998 | 3.8639 | 13.1 |
| 20 | 24.261 | 3.6656 | 20.0 |
| 21 | 24.713 | 3.5995 | 17.3 |
| 22 | 24.930 | 3.5686 | 14.4 |
| 23 | 25.622 | 3.4739 | 14.8 |
| 24 | 26.922 | 3.3090 | 14.6 |
| 25 | 27.220 | 3.2734 | 10.6 |
| 26 | 28.010 | 3.1829 | 22.1 |
| 27 | 28.324 | 3.1483 | 26.0 |
| 28 | 29.410 | 3.0344 | 7.5 |
| 29 | 29.942 | 2.9817 | 11.6 |
| 30 | 30.854 | 2.8957 | 5.3 |
| 31 | 31.459 | 2.8414 | 2.1 |
| 32 | 32.250 | 2.7735 | 3.0 |
| 33 | 32.725 | 2.7342 | 2.5 |
| 34 | 33.082 | 2.7056 | 2.2 |
| 35 | 33.379 | 2.6822 | 3.6 |
| 36 | 34.167 | 2.6221 | 3.6 |
| 37 | 35.525 | 2.5249 | 2.7 |
| 38 | 35.902 | 2.4993 | 3.0 |
| 39 | 36.988 | 2.4283 | 2.6 |
| 40 | 37.462 | 2.3987 | 3.3 |

In some embodiments according to the present disclosure, the Crystal Form A of Compound 1 has a differential scanning calorimetry curve having onset point of endothermic peak at 201.70° C.±2° C.

In some embodiments according to the present disclosure, the Crystal Form A of Compound 1 has a DSC pattern as shown in FIG. 2.

In some embodiments according to the present disclosure, the Crystal Form A of Compound 1 has a thermogravimetric analysis curve, wherein the weight loss at 100.00±2° C. is 0.02039%.

In some embodiments according to the present disclosure, the Crystal Form A of Compound 1 has a TGA pattern as shown in FIG. 3.

In another aspect, provided is a process for preparing the Crystal Form A, comprising adding Compound 1 into an alcohol solvent, a ketone solvent, an ether solvent, a mixed solvent of alcohol solvent and water, a mixed solvent of ketone solvent and water or a mixed solvent of ether solvent and water; heating for dissolution, and then cooling for crystallization to obtain the Crystal Form A.

In some embodiments according to the present disclosure, the alcohol solvent is selected from the group consisting of methanol, ethanol and isopropanol.

In some embodiments according to the present disclosure, the ketone solvent is selected from the group consisting of acetone and butanone.

In some embodiments according to the present disclosure, the ether solvent is selected from the group consisting of glycol dimethyl ether.

In some embodiments according to the present disclosure, the mixed solvent of alcohol solvent and water is selected from the group consisting of a mixed solvent of ethanol and water.

In some embodiments according to the present disclosure, in the mixed solvent of alcohol solvent and water, the volume ratio of alcohol solvent and water is selected from the group consisting of 1:0.2-1.5.

In yet another aspect, provided is use of the Crystal Form A of Compound 1 for the manufacture of a medicament for treating a disease associated with PDE4 receptor.

In some embodiments according to the present disclosure, the disease associated with PDE4 comprises psoriasis, psoriatic arthritis, chronic obstructive pneumonia, ankylosing spondylitis, inflammatory bowel disease.

Technical Effect

The Crystal Form A of Compound 1 has good stability, low hygroscopicity and promising druggability. The Crystal Form A of Compound 1 shows good stability in alcohol solvent, acetonitrile, acetone, ethyl acetate, tetrahydrofuran, mixed solvent of alcohol solvent and water, mixed solvent of acetonitrile and water or mixed solvent of acetone and water. Crystal Form A of Compound 1 shows good stability under accelerated condition of 40° C./Relative Humidity 75%. Crystal Form A of Compound 1 shows good stability at long-term condition of 25° C./Relative Humidity 60%.

Compound 1 shows excellent in vitro activity of inhibiting phosphodiesterase 4B subtype (PDE4B). Moreover, Compound 1 shows excellent in vitro activity of inhibiting TNFα production in hPBMC, which is superior over Apremilast. Compound 1 in the three dose groups of 0.3, 1 and 3 mg/kg significantly improves the symptoms of collagen-induced arthritis. In addition, Compound 1 in 1 mg/kg and 3 mg/kg dose groups, shows a significant improvement in arthritis pathology. The three dose groups show obvious dose-effect relationship in the arthritis pathology score. The therapeutic effect of Compound 1 at 3 mg/kg (clinical score and arthritis pathology score) is better than Apremilast at 5 mg/kg.

General Definition

Unless stated otherwise, the following terms and phrases have the following definitions. A specific term or phrase should not be considered as indefinite or unclear without specific definition and should be understood according to the normal meanings. A tradename used herein shall refer to the corresponding article or the active ingredient.

The intermediate compounds herein can be prepared by various synthesis processes well-known to a person skilled in the art, including the specific embodiments listed below, the embodiments by a combination with other chemical synthesis processes, and equivalent alternatives well known to a person skilled in the art. The preferable embodiments include but are not limited to the Examples below.

The chemical reaction of the specific embodiments is performed in a suitable solvent, and the solvent should be suitable for the chemical changes of the present disclosure and the required reagents and materials. To obtain the compound of the present disclosure, a person skilled in the art can modify or select a synthesis step or a reaction scheme based on the available embodiments.

The present disclosure will be described in a detailed manner and the Examples should be not considered as limitation thereto.

The solvents used herein are commercially available and can be used without further purification.

The following abbreviations are used: DMF: dimethylformamide; MsOH: methane sulfonic acid; EtOH: ethanol; NaOH: sodium hydroxide.

The compounds are named manually or by ChemDraw® software. The compound names on catalog by the providers are used.

X-ray Powder Diffractometer, XRPD
  Device: BRUKER D8 advance X-Ray diffractometer
  Testing method: about 10-20 mg of sample is used for XRPD detection.
    Detailed XRPD parameters are as follows:
    Light tube: Cu, kα, (λ=1.54056 Å).
    Light tube voltage: 40 kV, Light tube current: 40 mA
    Divergence slit: 0.60 mm
    Detector slit: 10.50 mm
    Anti-scatter slit: 7.10 mm
    Scanning range: 4-40 deg
    Step size: 0.02 deg
    Time/step: 0.12 s
    Sample stage spinning speed: 15 rpm
Differential Scanning Calorimeter, DSC
  Device: TA Q2000 Differential Scanning calorimeter
  Testing method: The sample (about 1 mg) is placed in DSC aluminum pot for testing, under 50 mL/min $N_2$, is heated from 25° C. to 350° C. at the heating rate of 10° C./min.
Thermal Gravimetric Analyzer, TGA
  Device: TA Q5000IR Thermal Gravimetric Analyzer
  Testing method: The sample (2-5 mg) is placed in TGA platinum pot for testing, under 25 mL/min $N_2$, is heated from room temperature to 350° C. at the heating rate of 10° C./min.
Dynamic Vapor Sorption, DVS
  Device: SEM Advantage-1 Dynamic Vapor Sorption apparatus
  Testing conditions: The sample (10-20 mg) is placed in DVS sample disk for testing.
    Detailed DVS parameters are as follows:
    Temperature: 25° C.
    Balance: dm/dt=0.01%/min (min: 10 min, max: 180 min)
    Drying: drying at 0% RH for 120 min
    RH (%) testing gradient: 10%
    RH (%) testing gradient range: 0% -90%-0%
    The hygroscopicity is categorized as follows:

| Hygroscopic Category | ΔW % |
| --- | --- |
| Deliquesce | Absorbing enough water to form liquid |
| Very hygroscopic | ΔW % ≥ 15% |
| Hygroscopic | 15% > ΔW % ≥ 2% |
| Slightly hygroscopic | 2% > ΔW % ≥ 0.2% |
| Not or little hygroscopic | ΔW % < 0.2% |

Note:
ΔW % refers to hygroscopic weight gain of the testing sample at 25 ± 1° C. and 80 ± 2% RH Content Determination Method
  Device: Agilent 1260 High Performance Liquid Chromatograph with DAD detector or Shimadzu LC-20A High Performance Liquid Chromatograph with PDA detector
    Detailed Chromatographic parameters are as follows:
    Chromatographic column: Agilent Eclipse plus C18 (4.6 mm×150 mm, 3.5 μm)
    Column temperature: 40° C.
    Flow rate: 1.0 mL/min
    Detecting wavelength: 230 nm
    Injection volume: 10 μL
    Running time: 60 min
    Mobile Phase A: 0.04% trifluoroacetic acid aqueous solution (V/V)
    Mobile Phase B: acetonitrile
    Diluent: acetonitrile: purified water=3:1 (v/v)
    Probe Wash: acetonitrile: purified water=3:1 (v/v)

Gradient elution procedure:

| Time (min) | Mobile Phase A (%) | Mobile Phase B (%) |
| --- | --- | --- |
| 0.00 | 85 | 15 |
| 30.00 | 70 | 30 |
| 50.00 | 30 | 70 |
| 55.00 | 15 | 85 |
| 55.01 | 85 | 15 |
| 60.00 | 85 | 15 |

EXAMPLES

Figure 1:
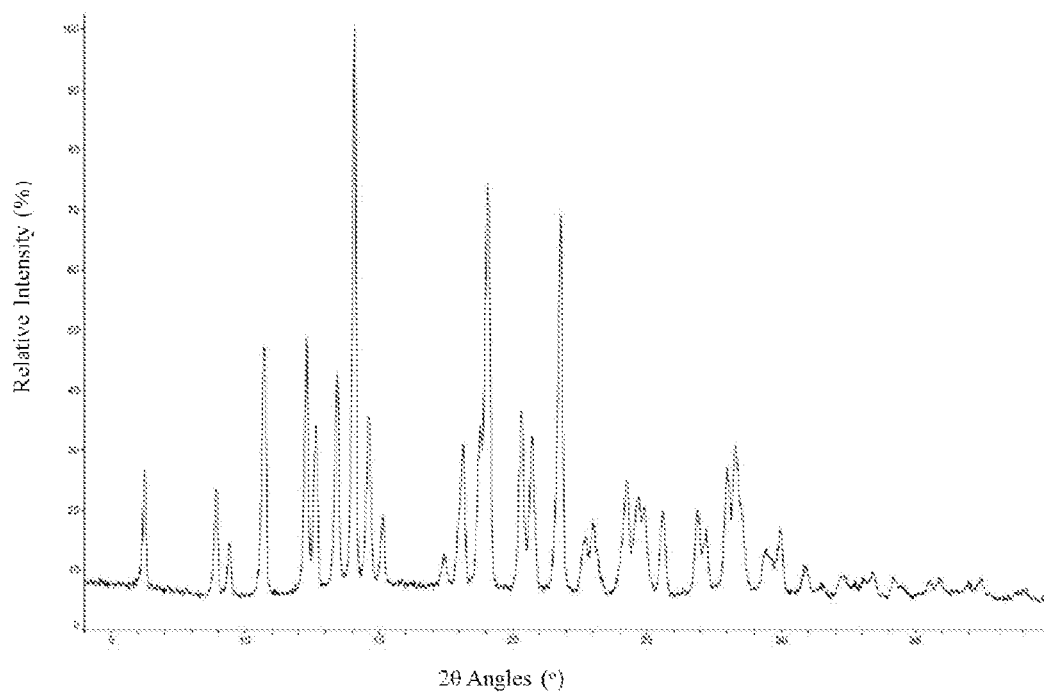
FIG. 1 shows the XRPD pattern by Cu-Kα radiation of the Crystal Form A of Compound 1.

The following Examples are provided for further illustration for the purpose of better understanding of the present disclosure. The specific embodiments should not be understood as limitation to the present disclosure.

Example 1

Preparation of Crystal Form A of Compound 1

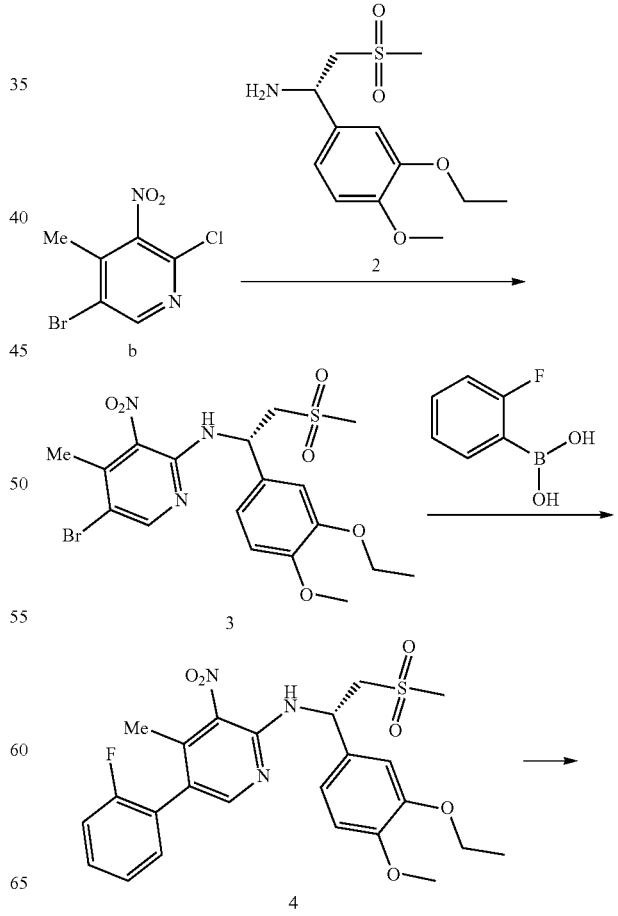

-continued

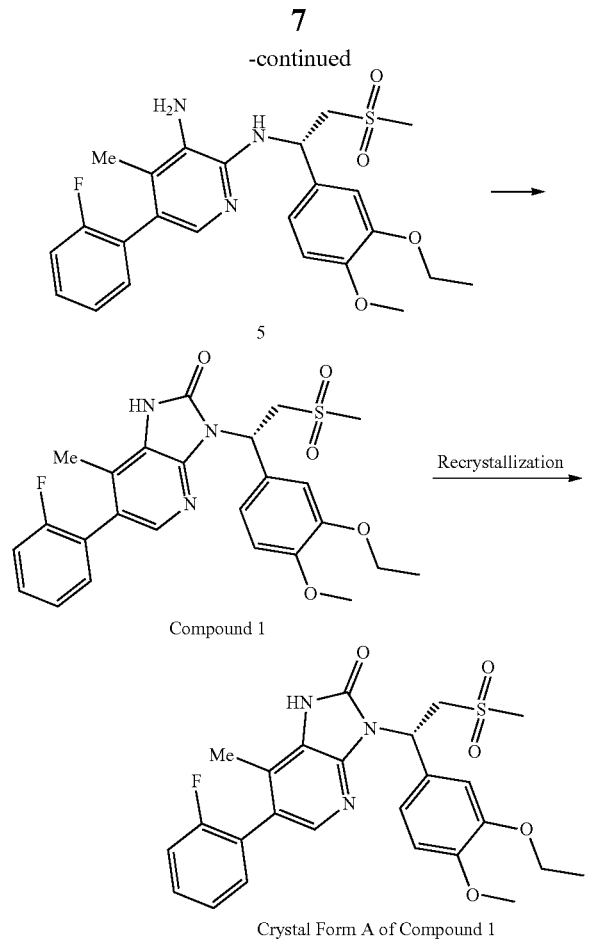

Compound 1

Crystal Form A of Compound 1

Step 1: Synthesis of Compound 3

At room temperature, Compound b (10.00 g, 39.77 mmol), Compound 2 (9.78 g, 35.79 mmol) and diisopropylamine (10.28 g, 79.53 mmol, 13.89 mL) were dissolved in N,N-dimethylformamide (200.00 mL), which was purged with nitrogen for three times, and the reaction mixture was heated to 120° C. under nitrogen protective atmosphere with stirring for 16 h. After the reaction was completed, the reaction mixture was cooled to room temperature, added with water (400 mL), and extracted with ethyl acetate (200 mL×3). The organic phases were combined and washed with saturated saline solution (100 mL×3), dried over anhydrous sodium sulfate, and filtered to remove drying agent. The filtrate was concentrated under reduced pressure. The residue was subjected to column chromatography (eluent: ethyl acetate/petroleum ether=1/4–1/2, volume ratio) to give the target Compound 3.

MS-ESI m/z: 509.8 [M+Na]$^+$, 511.8 [M+Na+2]$^+$. $^1$H NMR (400 MHz, CDCl$_3$) δ: 8.27 (s, 1H), 7.27 (d, J=6.8 Hz, 1H), 6.90-6.86 (m, 2H), 6.81 (d, J=8.0 Hz, 1H), 5.72 (q, J=6.4 Hz, 1H), 4.04 (q, J=6.8 Hz, 2H), 3.80 (s, 3H), 3.68 (dd, J=6.6, 14.6 Hz, 1H), 3.40 (dd, J=6.4, 14.8 Hz, 1H), 2.52 (s, 3H), 2.45 (s, 3H), 1.40 (t, J=7.0 Hz, 3H).

Step 2: Synthesis of Compound 4

At room temperature, Compound 3 (12.10 g, 24.78 mmol) and o-fluorophenylboronic acid (5.20 g, 37.17 mmol) were dissolved in dioxane (150.00 mL) and water (50.00 mL), then potassium carbonate (10.27 g, 74.34 mmol) and [1,1'-bis(diphenylphosphino)ferrocene] palladium dichloride dichloromethane complex (2.02 g, 2.48 mmol) were added under nitrogen protective atmosphere. The reaction mixture was heated to under nitrogen protective atmosphere to 80° C. with stirring for 14 h. After the reaction was completed, the reaction mixture was cooled to room temperature, added with water (500 mL), and extracted with ethyl acetate (300 mL×3). The organic phases were combined, dried over anhydrous sodium sulfate, and filtered to remove drying agent. The filtrate was concentrated under reduced pressure. The residue was subjected to column chromatography (eluent:ethyl acetate/petroleum ether=1/10–1/4, volume ratio) to give the target Compound 4.

MS-ESI m/z: 504.1 [M+H]$^+$. $^1$H NMR (400 MHz, CDCl$_3$) δ: 8.07 (s, 1H), 7.42 (d, J=6.8 Hz, 1H), 7.38-7.30 (m, 1H), 7.18-7.06 (m, 3H), 6.98-6.89 (m, 2H), 6.83 (d, J=8.4 Hz, 1H), 5.82 (q, J=6.6 Hz, 1H), 4.13-4.00 (m, 3H), 3.81 (s, 3H), 3.43 (dd, J=6.4, 14.7 Hz, 1H), 2.55 (s, 3H), 2.23 (s, 3H), 1.41 (t, J=7.0 Hz, 3H).

Step 3: Synthesis of Compound 5

At room temperature, to Compound 4 (9.20 g, 18.27 mmol) and ammonium chloride (9.77 g, 182.70 mmol) was added methanol (200.00 mL), and zinc powder (11.95 g, 182.70 mmol) was added in 20 batches at 0° C. The reaction mixture was stirred at 0° C. for 16 h. After the reaction was completed, the reaction mixture was filtered to remove zinc powder, and the filtrate was concentrated under reduced pressure to obtain residue. The residue was dissolved in dichloromethane (200 mL). The suspension was filtered to remove the insolubles, and the filtrate was concentrated under reduced pressure to give Compound 5.

MS-ESI m/z: 474.0 [M+H]$^+$. $^1$H NMR (400 MHz, CDCl$_3$) δ: 7.55 (s, 1H), 7.42-7.32 (m, 1H), 7.20 (d, J=4.8 Hz, 2H), 7.13 (t, J=9.0 Hz, 1H), 7.08-7.03 (m, 2H), 6.88 (d, J=8.8 Hz, 1H), 5.70 (s, 1H), 4.19-4.07 (m, 2H), 4.00-3.90 (m, 1H), 3.87 (s, 3H), 3.58 (dd, J=6.0, 14.4 Hz, 1H), 2.78 (s, 3H), 2.05 (s, 3H), 1.47 (t, J=7.2 Hz, 3H).

Step 4: Synthesis of Compound 1

At room temperature, Compound 5 (9.30 g, 19.64 mmol) and triethylamine (19.87 g, 196.40 mmol) were dissolved in tetrahydrofuran (200.00 mL). The reaction mixture was cooled to 0° C. and added dropwise with a solution of triphosgene (2.33 g, 7.86 mmol) in tetrahydrofuran (50.00 mL). The tetrahydrofuran (50.00 mL) solution was added dropwise to the above reaction solution. After addition, the reaction mixture was stirred at 0° C. for 3 h under nitrogen protective atmosphere. After the reaction was completed, the reaction mixture was added with water (200 mL) and extracted with ethyl acetate (100 mL×3). The organic phases were combined, dried over anhydrous sodium sulfate, and filtered to remove drying agent. The filtrate was concentrated under reduced pressure. The residue was subjected to column chromatography (eluent: ethyl acetate/petroleum ether=1/3–2/1, volume ratio) to give Compound 1.

$^1$H NMR (400 MHz, CDCl$_3$) δ: 10.13-10.01 (m, 1H), 7.87 (s, 1H), 7.39-7.32 (m, 1H), 7.31 (d, J=1.6 Hz, 1H), 7.18-7.15 (m, 3H), 7.11 (t, J=9.2 Hz, 1H), 6.74 (d, J=8.4 Hz, 1H), 6.14 (dd, J=4.8, 9.6 Hz, 1H), 4.86 (dd, J=9.4, 14.6 Hz, 1H), 4.09-3.97 (m, 2H), 3.88 (dd, J=4.4, 14.8 Hz, 1H), 3.76 (s, 3H), 2.70 (s, 3H), 2.16 (s, 3H), 1.35 (t, J=7.0 Hz, 3H).

Step 5: Preparation of Crystal Form A of Compound 1

At room temperature, to Compound 1 (6.45 g, 12.91 mmol) were added water (160.00 mL) and ethanol (170.00 mL), and the reaction mixture was stirred at 90° C. for 0.5 h. The reaction solution gradually became clear during stirring. The reaction mixture was slowly cooled to 20° C. while stirring, and stirring was continued at 20° C. for 16 h, during which many white solids precipitated. The white solids were collected by filtration and dried in vacuum oven at 45° C. for 18 h to give Crystal Form A of Compound 1.

MS-ESI m/z: 500.2 [M+H]$^+$. $^1$H NMR (400 MHz, CDCl$_3$) δ: 9.97 (s, 1H), 7.94 (s, 1H), 7.46-7.39 (m, 1H), 7.38 (d, J=1.6 Hz, 1H), 7.26-7.22 (m, 3H), 7.17 (t, J=9.0 Hz, 1H), 6.81 (d, J=8.0 Hz, 1H), 6.22 (dd, J=4.8, 9.6 Hz, 1H), 4.93 (dd, J=9.6, 14.8 Hz, 1H), 4.13-4.03 (m, 2H), 3.95 (dd, J=4.8, 14.8 Hz, 1H), 3.83 (s, 3H), 2.77 (s, 3H), 2.23 (s, 3H), 1.42 (t, J=7.0 Hz, 3H).

Experimental Example 1

Stability Tests of Crystal Form A in Different Solvents 50 mg of Crystal Form A in multiple portions were added into single solvent or mixed solvents in the following table, stirred at 40° C. for 2 days and centrifuged. The solids in all samples were collected and dried in vacuum drying oven (40° C.) overnight. The crystal forms were tested for XRPD. The results were shown in Table 2.

TABLE 2

Stability tests of Crystal Form A in different solvents

| No. | Solvent | Solvent Added (mL) | Status (after 2 days) | Crystal Form |
|---|---|---|---|---|
| 1 | Methanol | 0.4 | Suspension | Crystal Form A |
| 2 | Ethanol | 0.4 | Suspension | Crystal Form A |
| 3 | Acetonitrile | 0.4 | Suspension | Crystal Form A |
| 4 | Acetone | 0.4 | Suspension | Crystal Form A |
| 5 | Ethyl Acetate | 0.4 | Suspension | Crystal Form A |
| 6 | Tetrahydrofuran | 0.3 | Suspension | Crystal Form A |
| 7 | Methanol:Water (3:1) | 0.4 | Suspension | Crystal Form A |
| 8 | Ethanol:Water (3:1) | 0.4 | Suspension | Crystal Form A |
| 9 | Acetonitrile:Water (1:1) | 0.4 | Suspension | Crystal Form A |
| 10 | Acetone:Water (1:2) | 0.4 | Suspension | Crystal Form A |

Conclusion: The Crystal Form A of Compound 1 shows good stability in alcohol solvent, acetonitrile, acetone, ethyl acetate, tetrahydrofuran, mixed solvent of alcohol solvent and water, mixed solvent of ketone solvent and water, mixed solvent of acetonitrile and water, or mixed solvent of acetone and water.

Experimental Example 2

Hygroscopicity test of Crystal Form A of Compound 1 Materials

Figure 4:
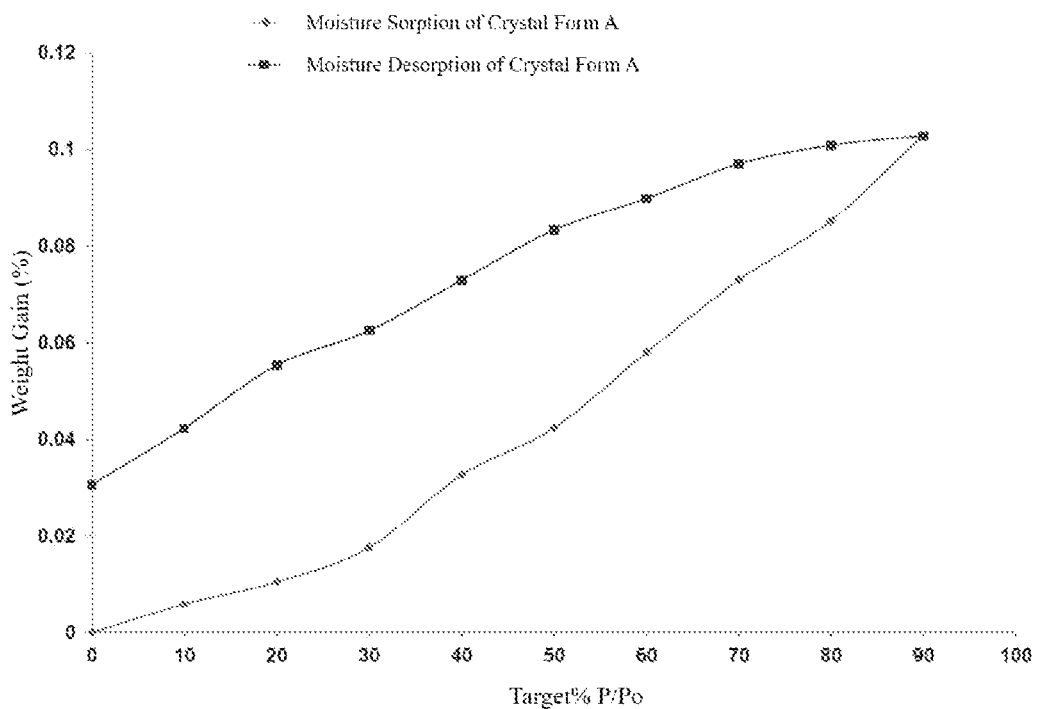
FIG. 4 shows the DVS pattern of the Crystal Form A of Compound 1.

SEM DVS Advantage-1 Dynamic Vapor Sorption instrument
Procedures:
10-20 mg of Crystal Form A of Compound 1 was placed in DVS sample disk for testing.
Results:
The DVS pattern of Crystal Form A of Compound 1 was shown in FIG. 4, ΔW=0.08%.
Conclusion:
Crystal Form A of Compound 1 had a hygroscopic weight gain of 0.08% at 25° C. and 80% RH, which was less than 0.2%, showing no or little hygroscopicity.

Experimental Example 3

Solid stability Tests of Crystal Form A of Compound 1 at High Temperature, High Humidity and Strong Light Conditions According to "Guidelines for Stability Test of APIs and Preparations" (Chinese Pharmacopoeia 2015 Edition Four General Principles 9001), Crystal Form A of Compound 1 was tested for stability at high temperature (60° C., open), high humidity (room temperature/Relative Humidity 92.5% Open) and strong light (4500±500 lux, 90 μw/cm$^2$, sealed).

1.5 g of Crystal Form A of Compound 1 was weighed and placed in an open watch glass and spread into a thin layer. The samples placed under high temperature and high humidity conditions were placed in a desiccator for inspection, and the samples were taken on the 5$^{th}$, 10$^{th}$ and 30$^{th}$ days for testing, and the test results were compared with the initial test results of day 0. The samples placed under strong light were covered with a transparent lid with a sealing film, and the samples were taken on the 5$^{th}$ and 10$^{th}$ days for testing, and the test results were compared with the initial test results on day 0. The test results were shown in the following Table 3.

TABLE 3

Solid stability test results of Crystal Form A of Compound 1 under high temperature, high humidity and strong light conditions

| Test Conditions | Sampling Time Point | Appearance | Content | Total Impurity |
|---|---|---|---|---|
| — | Day 0 | White powder | 99.5% | 0.11% |
| High temperature (60° C., Open) | Day 5 | White powder | 99.2% | 0.16% |
| | Day 10 | White powder | 98.8% | 0.16% |
| | Day 30 | White powder | 99.0% | 0.16% |
| High humidity (Room Temperature/ Relative Humidity 92.5%, Open) | Day 5 | White powder | 99.0% | 0.16% |
| | Day 10 | White powder | 98.9% | 0.16% |
| | Day 30 | White powder | 99.0% | 0.16% |
| Strong light (4500 ± 500 lux, 90 μw/cm$^2$, Sealed) | Day 5 | White powder | 98.8% | 0.11% |
| | Day 10 | White powder | 98.6% | 0.11% |

Conclusion: The Crystal Form A of Compound 1 showed good stability under high temperature, high humidity or strong light conditions Experimental Example 4: Solid stability test of Crystal Form A of Compound 1 under accelerated conditions According to "Guidelines for Stability Test of APIs and Preparations" (Chinese Pharmacopoeia 2015, Volume IV, General Principles 9001), Crystal Form A of Compound 1 was tested for stability under high temperature and high humidity accelerated conditions (40 ° C./Relative Humidity 75%, sealed).

1.4 g of Crystal Form A of Compound 1 was weighed and placed in a double-layer low-density polyethylene bag. Each layer of the low-density polyethylene bag was buckled and sealed respectively and then the bag was placed in an aluminum foil bag and heat-sealed. The samples were taken on the 1$^{st}$, 2$^{nd}$, 3$^{rd}$ and 6$^{th}$ months for testing, and the test results were compared with the initial test results of day 0. The test was repeated three times, with different batch of Crystal Form A of Compound 1 for each time. The test results were shown in the following Table 4.

TABLE 4

Solid stability test results of Crystal Form A of Compound 1 under accelerated conditions (40° C./Relative Humidity 75%, sealed)

| Test Conditions | Batch | Sampling Time Point | Appearance | Content | Total Impurity | Crystal Form (XRPD) |
|---|---|---|---|---|---|---|
| — | 1 | Day 0 | White powder | 99.4% | 0.09% | Crystal Form A |
| 40° C./Relative Humidity 75%, Sealed | | 1$^{st}$ month | White powder | 99.3% | 0.09% | Not detected |
| | | 2$^{nd}$ month | White powder | 99.1% | 0.09% | Not detected |
| | | 3$^{rd}$ month | White powder | 99.5% | 0.09% | Not detected |
| | | 6$^{th}$ month | White powder | 100.1% | 0.10% | Crystal Form A |
| — | 2 | Day 0 | White powder | 99.4% | 0.10% | Crystal Form A |
| 40° C./Relative Humidity 75%, Sealed | | 1$^{st}$ month | White powder | 99.1% | 0.11% | Not detected |
| | | 2$^{nd}$ month | White powder | 99.0% | 0.11% | Not detected |
| | | 3$^{rd}$ month | White powder | 99.2% | 0.10% | Not detected |
| | | 6$^{th}$ month | White powder | 100.5% | 0.12% | Crystal Form A |
| — | 3 | Day 0 | White powder | 99.5% | 0.11% | Crystal Form A |
| 40° C./Relative Humidity 75%, Sealed | | 1$^{st}$ month | White powder | 98.8% | 0.16% | Not detected |
| | | 2$^{nd}$ month | White powder | 98.9% | 0.16% | Not detected |
| | | 3$^{rd}$ month | White powder | 99.2% | 0.16% | Not detected |
| | | 6$^{th}$ month | White powder | 100.0% | 0.11% | Crystal Form A |

Conclusion: The Crystal Form A of Compound 1 showed good stability under accelerated conditions of 40° C./Relative Humidity 75%.

Experimental Example 5

Solid Stability Test of Crystal Form A of Compound 1 Under Long-Term Conditions

According to "Guidelines for Stability Test of APIs and Preparations" (Chinese Pharmacopoeia 2015, Volume IV, General Principles 9001), Crystal Form A of Compound 1 was tested for stability under long-term conditions (25° C./Relative Humidity 60% sealed).

1.4 g of Crystal Form A of Compound 1 was weighed and placed in a double-layer low-density polyethylene bag. Each layer of the low-density polyethylene bag was buckled and sealed respectively and then the bag was placed in an aluminum foil bag and heat-sealed. The samples were taken on the 3$^{rd}$, 6$^{th}$, 9$^{th}$, 12$^{th}$ and 18$^{th}$ months for testing and the test results were compared with the initial test results of day 0. The test was repeated three times, with different batch of Crystal Form A of Compound 1 for each time. The test results were shown in following Table 5.

TABLE 5

Solid stability test results of Crystal Form A of Compound 1 under long-term conditions (25° C./Relative Humidity 60%, sealed)

| Testing Conditions | Batch | Sampling Time Point | Appearance | Content | Total Impurity | Crystal Form (XRPD) |
|---|---|---|---|---|---|---|
| — | 1 | Day 0 | White powder | 99.4% | 0.09% | Crystal Form A |
| 25° C./Relative Humidity 60%, Sealed | | 3$^{rd}$ month | White powder | 99.0% | 0.09% | Not detected |
| | | 6$^{th}$ month | White powder | 101.4% | 0.09% | Crystal Form A |
| | | 9$^{th}$ month | White powder | 99.6% | 0.09% | Not detected |
| | | 12$^{th}$ month | White powder | 98.8% | 0.08% | Crystal Form A |
| | | 18$^{th}$ month | White powder | 97.3% | 0.10% | Not detected |
| — | 2 | Day 0 | White powder | 99.4% | 0.10% | Crystal Form A |
| 25° C./Relative Humidity 60%, Sealed | | 3$^{rd}$ month | White powder | 100.5% | 0.11% | Not detected |
| | | 6$^{th}$ month | White powder | 100.1% | 0.12% | Crystal Form A |
| | | 9$^{th}$ month | White powder | 99.6% | 0.11% | Not detected |
| | | 12$^{th}$ month | White powder | 98.2% | 0.09% | Crystal Form A |
| | | 18$^{th}$ month | White powder | 99.1% | 0.11% | Not detected |
| — | 3 | Day 0 | White powder | 99.5% | 0.11% | Crystal Form A |
| 25° C./Relative Humidity 60%, Sealed | | 3$^{rd}$ month | White powder | 98.9% | 0.16% | Not detected |
| | | 6$^{th}$ month | White powder | 98.5% | 0.12% | Crystal Form A |
| | | 9$^{th}$ month | White powder | 99.2% | 0.11% | Not detected |
| | | 12$^{th}$ month | White powder | 98.4% | 0.10% | Crystal Form A |
| | | 18$^{th}$ month | White powder | 99.7% | 0.17% | Not detected |

Conclusion: The Crystal Form A of Compound 1 showed good stability under long-term conditions of 25° C./Relative Humidity 60%.

Testing Example 1

Inhibitory Activity of Compound 1 on Phosphodiesterase 4B Subtype (PDE4B Enzyme)

This biological experiment based on fluorescence polarization was used to determine AMP/GMP expression, that is, to show enzyme activity by tracking AMP/GMP antibody binding.

Agents:

Experimental buffer solution: 10 mM Trihydroxymethyl aminomethane-hydrochloric acid buffer solution (Tris-HCl) (pH 7.5), 5 mM $MgCl_2$, 0.01% Polyoxyethylene lauryl ether (Brij 35), 1 mM Dithiothreitol (DTT), and 1% DMSO.

Enzymes: Recombinant humanized PDE4B (Genebank Accession Number NM_002600; amino acid 305 terminal) was expressed with baculovirus in Sf9 insect cells using N-terminal GST tag. MW=78 kDa.

Enzyme substrate: 1 μM cAMP

Detection: Transcreener®AMP2/GMP2 antibody and AMP2/ GMP2 AlexaFluor633 tracing.

Procedures:
1. Dissolving the recombinant human PDE4B enzyme and enzyme substrate (1 μM cAMP) in freshly prepared experimental buffer;
2. Transferring the above PDE4B enzyme buffer solution to reaction wells;
3. Adding Compound 1 dissolved with 100% DMSO to the reaction well with PDE4B enzyme buffer solution via acoustic technology (echo 550 nanoliter range) and incubating for 10 min at room temperature;
4. Then, adding the enzyme substrate buffer solution to the above reaction wells to initiate the reaction;
5. Incubating for 1 h at room temperature;
6. Adding the detection mixture (Transcreener®AMP2/GMP2 antibody and AMP2/GMP2 AlexaFluor633 tracing) to terminate the reaction and incubating for 90 min with slow mixing. The range of fluorescence polarization determination is Ex/Em=620/688.

Data Analysis: The fluorescence polarization signal was converted into nM according to the AMP/GMP standard curve and the control % enzyme activity relative to the DMSO calculated by Excel software. The Curve was fit with GraphPad Prism (drawing medical icons).

TABLE 6

Results of in vitro screening test of compound according to the present disclosure

| Compound | IC50 (nM) |
|---|---|
| Compound 1 | 0.685 |

Conclusion: Compound 1 showed excellent in vitro activity of inhibiting phosphodiesterase 4B subtype (PDE4B).

Testing Example 2

Evaluation of Inhibition of TNFα Production in Human Peripheral Blood Mononuclear Cells (hPBMC) In Vitro The inhibitory activity of Compound 1 of lipopolysaccharide (LPS)-induced TNFα production in human peripheral blood mononuclear cells.

Procedures:
1. Collecting normal human whole blood, which was anticoagulated with EDTA-K2 anticoagulation tube;
2. Separating PBMC with Ficoll density gradient centrifugation, counting and adjusting the cell concentration to $2\times10^6$/mL;
3. To U-bottom 96-well plate were added $2\times10^5$ cells/well, LPS 1 ng/mL was added, various concentrations of compound at 100 μM, 10 μM, 1 μM, 100 nM, 10 nM, 1 nM, 100 pM, 10 pM, 200 μl system/well, in duplicated wells;
4. Incubating for 24 h, collecting the supernatant;
5. Detecting the level of TNFα in supernatant with ELISA, fitting the inhibition curve and calculating IC50 with Graphpad Prism software.

TABLE 7

Inhibitory activity of compound according to the present disclosure on TNFα production in hPBMC

| Compound | IC50(nM) | Compound | IC50(nM) |
|---|---|---|---|
| Apremilast | 16.5 (n = 3) | Compound 1 | 0.56 (n = 2) | n represents test times.

Conclusion: Compound 1 showed excellent in vitro activity of inhibiting TNFα production in hPBMC, which was superior over Apremilast.

Testing Example 3

In Vivo CIA Model

Object:

The collagen-induced mice arthritis model is an animal model used to evaluate the efficacy of drug treatment of psoriatic arthritis, and the pathogenesis and symptoms are significantly correlated with psoriatic arthritis. A series of symptoms similar to human psoriatic arthritis, such as redness and swelling of the joint, articular cartilage damage, and capsula articularis damage are elicited in the model by injection of type II collagen to activate reactivity of B cells, T cell on bone collagen, and the activated B cells and T cells enter the joints to cause joint inflammation. During preclinical evaluation of candidate compounds for treating psoriatic arthritis, collagen-induced arthritis in mice is often used to evaluate the effectiveness.

The purpose of this experiment was to study the therapeutic effect of Compound 1 on collagen-induced arthritis in mice, so as to provide preclinical pharmacodynamic relevant information for subsequent clinical studies.

Procedures:

1. Type II collagen/complete Freund's adjuvant immunization

Preparation of acetic acid: Diluting acetic acid to 100 mM, which was filtered with 0.22 um filter membrane and stored at 4° C.

Bovine type II collagen solution: Dissolving bovine type II collagen (CII) in acetic acid solution, which was stored at 4° C. overnight.

Preparation of emulsion: Mixing the CII solution stored overnight with equal volume of the complete Freund's adjuvant and homogenize the mixture with high-speed homogenizer until the solution formed a stable emulsion.

Preparation of lipopolysaccharide (LPS): Weighing LPS, adding normal saline, and mixing until a stable solution with concentration of 0.3 mg/kg was formed.

2. Induction of Arthritis:

The mice were randomly assigned to different treatment groups. The day of the first immunization was recorded as day 0, and the subsequent days were marked sequentially.

After DBA/1 mice were anesthetized with isoflurane, the prepared collagen emulsion was injected subcutaneously in the tail.

On day 23, 100 μl of LPS solution was injected intraperitoneally.

Normal group mice were free of immunization.

3. Administration and Dosage Design

On day 27, when the average clinical score reached about 1, 60 mice with moderate onset were selected, and they were re-randomized according to body weight and score, with 10 mice in each group.

Dexamethasone as positive control drug in 0.3 mg/kg dose group is commonly used in the CIA model. In addition, the relevant dose design of Compound 1 and the control compound Apremilast were determined according to the results of earlier preliminary experiments. Group 1 was normal mice without any treatment; Group 2 was vehicle control group and was administered vehicle; Group 3 was administered dexamethasone at a dose of 0.3 mg/kg; Group 4 was administered Apremilast at a dose of 5 mg/kg; Group 5, Group 6, and Group 7 were administered Compound 1 with doses of 0.3, 1, and 3 mg/kg, respectively. Administration was given once a day for 11 days in total. The volume of intragastric administration was 10 ml/kg.

TABLE 8

Grouping and dose design

| Group | Tested drug | Number | Administration Route | Concentration mg/mL | Dose mg/kg | Administration Frequency |
|---|---|---|---|---|---|---|
| 1 | Normal group | 5 | N/A. | N/A | N/A | N/A |
| 2 | Vehicle | 10 | Gavage | N/A | N/A | 1/day, 11 days |
| 3 | Dexamethasone | 10 | Gavage | 0.03 | 0.3 | 1/day, 11 days |
| 4 | Apremilast | 10 | Gavage | 0.5 | 5 | 1/day, 11 days |
| 5 | Compound 1 | 10 | Gavage | 0.03 | 0.3 | 1/day, 11 days |
| 6 | Compound 1 | 10 | Gavage | 0.1 | 1 | 1/day, 11 days |
| 7 | Compound 1 | 10 | Gavage | 0.3 | 3 | 1/day, 11 days |

4. Determination of Incidence Index of Arthritis

Clinical observation: From 7 days before immunization to 23 days after immunization, the basic health status and body weight changes of DBA/1 mice were observed daily (recorded once a week). After the 23$^{rd}$ day, the health status, morbidity and body weight change of the mice were observed daily (recorded at least three times a week) until the end of the experiment.

Clinical score: After LPS injection, the morbidities of mice were observed every day. After the onset of disease in mice (clinical symptoms of arthritis), they were scored according to severity of conditions (redness and swelling, joint deformation) according to 0-4 point standard, with a maximum score of 4 for each limb, and a maximum score of 16 for each animal. The scoring standard was shown in Table 9. At least three times of scoring were performed a week.

TABLE 9

Arthritis clinical scoring standard

| Score | Clinical symptoms |
|---|---|
| 0 | No erythema and redness and swelling |
| 1 | Erythema or mild redness and swelling near the tarsal bone or ankle joint or metatarsal bone, 1 toe with redness and swelling |
| 2 | Slight erythema and swelling for ankle joint and metatarsal bone, or more than two toes with redness and swelling |
| 3 | Moderate erythema and swelling for ankle joint, wrist joint and metatarsal bone |
| 4 | Severely redness and swelling for all of ankle joints, wrist joints, metatarsal bone and toes |

Pathology: On day 38, the mouse was euthanized. The two posterior limbs of the mouse were taken, soaked with 10% formalin solution, decalcified with formic acid solution, embedded with paraffin, sectioned, stained with hematoxylin-eosin (HE), and observed with photomicrography. The degree of joint damage was evaluated in four aspects: inflammatory cell infiltration, pannus formation, cartilage injury and bone resorption, and scored according to 0-4 score standard. The scoring standard was shown in Table 10:

TABLE 10

Arthritis Pathology Scoring Standard

| Lesion | Lesion Characteristics | Score |
|---|---|---|
| Inflammatory cell infiltration | No visible inflammatory cells | 0 |
| | Fibrosis of cells under the synovium, with minimal cell infiltration | 1 |
| | Synovial cell hyperplasia, with small amount of monocyte infiltration | 2 |
| | Synovial cell hyperplasia, with massive monocytes, plasma cells, lymphocyte infiltration | 3 |
| | Infiltration of large number of inflammatory cells around the joint, tissue fibrosis, thickening of the synovium | 4 |
| Pannus formation | No visible pannus formation | 0 |
| | Minimal pannus formation on the edge of cartilage | 1 |
| | Fibrous tissue hyperplasia between cartilages, with small amount of pannus formation at the edge of the joint | 2 |
| | Pannus formation on 50% of articular cartilage surface | 3 |

TABLE 10-continued

Arthritis Pathology Scoring Standard

| Lesion | Lesion Characteristics | Score |
|---|---|---|
| | Pannus formation on the entire surface of articular cartilage | 4 |
| Cartilage injury | No visible cartilage injury | 0 |
| | Articular chondrocyte hyperplasia | 1 |
| | Chondrocyte matrix lost, with small amount of chondrocytes destroyed | 2 |
| | Fibrous tissue hyperplasia around joints, with large number of chondrocytes destroyed | 3 |
| | A lot of fibrous tissue hyperplasia between articular cartilages, with cartilage erosion | 4 |
| Bone resorption | No visible bone resorption | 0 |
| | Minimal bone resorption at the edge of the synovium | 1 |
| | Small amount of osteoclast formation for small amount of bone tissues | 2 |
| | Bone tissues under local articular cartilage with bone resorption | 3 |
| | Bone resorption for wide range of bone tissues, with cartilage erosion | 4 |

5. Statistical Processing

The experimental data were expressed as mean±standard error (Mean±SEM), body weight and clinical score were analyzed by Two-way ANOVA, pathological score and AUC were analyzed by t test, and p<0.05 was considered as significant.

Experimental Results:

1. Clinical Score:

On the 25$^{th}$ day after the first immunization (Day 2 after the second immunization), the mice began to develop clinical symptoms of arthritis. Administration started on the 27$^{th}$ day. The average clinical score of the vehicle control group gradually increased and reached 8.3 points on the 36$^{th}$ day, indicating successful establishment of the collagen-induced arthritis model.

Compared with the vehicle control group, Compound 1 at 0.3, 1, and 3 mg/kg can significantly reduce the clinical score of arthritis mice at the experimental end point (37$^{th}$ day), and the clinical average scores at three doses dropped to 3.6 (p<0.0001), 4.3 (p<0.001) and 3.5 (p<0.0001). Therefore, Compound 1 can effectively reduce the collagen-induced arthritis at a dose as low as 0.3 mg/kg.0.3 mg/kg of dexamethasone group can significantly suppress the clinical score of the collagen-induced arthritis. From the 30$^{th}$ day, the clinical score was maintained at 0, which was significantly different from the vehicle control group (p<0.0001) and continued until the end of the experiment. 5 mg/kg of Apremilast group also suppressed the increase of clinical score, and showed significant difference from the vehicle control group from the 33$^{rd}$ day and continued until the end of the experiment. Till the 37$^{th}$ day, the average clinical symptom score was 4.2, which was decreased by 3.7 (p<0.001) as compared to the vehicle control group.

By analyzing the clinical score curve of each animal in each group, the area under the curve (AUC) was calculated. By the average value of the area under the curve between groups, the inhibition rate of each dose group relative to the vehicle control group was calculated. Compared with the vehicle control group, the dexamethasone group and the Apremilast group significantly reduced the clinical scores of the arthritis animals and the inhibition rates were 96.4% (p<0.0001) and 41.3% (p<0.05), respectively. Compound 1 at three doses of 0.3, 1, and 3 mg/kg can significantly reduce the area under the clinical score curve of the arthritis animals, and the inhibition rates were 43.9% (p<0.05), 39.4% (p<0.05) and 51.7% (p<0.01), respectively. Compound 1 at 1 mg/kg group had comparable inhibition rate as Apremilast at 5 mg/kg group (p<0.05 for both groups), while Compound 1 at 3 mg/kg group had better inhibition rates than Apremilast at 5 mg/kg group (p values were <0.01 and <0.05, respectively)

2. Histopathological Score

Two posterior limbs of each group of mice were taken as sections for H.E. staining, and the total score of both hind limbs was taken. The arthritis mice in the vehicle control group had a total pathological score of 20.20±1.15. Compared with the vehicle control group, the control compound Apremilast at a dose of 5 mg/kg can also significantly reduce the pathological score of the arthritis mice, which can be reduced to 13.90±1.89 (p<0.05). Compound 1 at the dose of 1 and 3 mg/kg can significantly reduce the pathological scores of the arthritis mice, which can be reduced to 14.00±2.43 (p<0.05) and 9.20±1.83 (p<0.0001), respectively. Compound 1 at 1 mg/kg group had comparable arthritis pathological score as that of Apremilast at 5 mg/kg (p<0.05 for both groups), while Compound 1 at 3 mg/kg group had better arthritis pathological score than that of Apremilast at 5 mg/kg group (p values as <0.0001 and <0.05, respectively).

3. Conclusion

Compound 1 at three dose groups of 0.3, 1 and 3 mg/kg significantly improved the symptoms of the collagen-induced arthritis.

There was significant improvement for arthritis pathology at 1 mg/kg and 3 mg/kg dose groups, and the three dose groups showed obvious dose-effect relationship in the arthritis pathological score. The therapeutic effect of Compound 1 at 3 mg/kg (clinical score and arthritis pathological score) was better than that of Apremilast at 5 mg/kg.

The invention claimed is:

1. The Crystal Form A of Compound 1, wherein the Crystal Form A has an X-ray powder diffraction pattern comprising characteristic diffraction peaks at the following 2θ angles: 10.69±0.2°, 12.31±0.2°, 13.45±0.2°, 14.10±0.2°, 14.62±0.2°, 19.07±0.2°, 20.33±0.2°, 21.79±0.2°, Compound 1

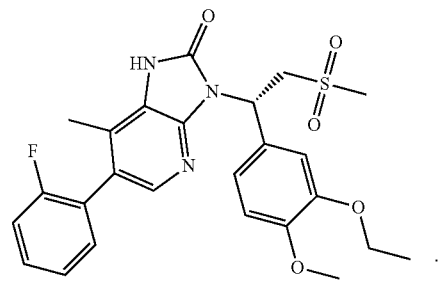

2. The Crystal Form A of Compound 1 according to claim 1, wherein the Crystal Form A has an X-ray powder diffraction pattern further comprising characteristic diffraction peaks at the following 2θ angles: 6.25±0.2°, 8.93±0.2°, 10.69±0.2°, 12.31±0.2°, 13.45±0.2°, 14.10±0.2°, 14.62±0.2°, 18.16±0.2°, 19.07±0.2°, 20.33±0.2°, 21.79±0.2°.

3. The Crystal Form A of Compound 1 according to claim 2, wherein
the Crystal Form A has an X-ray powder diffraction pattern as shown in FIG. 1.

4. The Crystal Form A of Compound 1 according to claim 1, wherein the Crystal Form A has a differential scanning calorimetry curve having onset point of endothermic peak at 201.70° C.±2° C.

Figure 2:
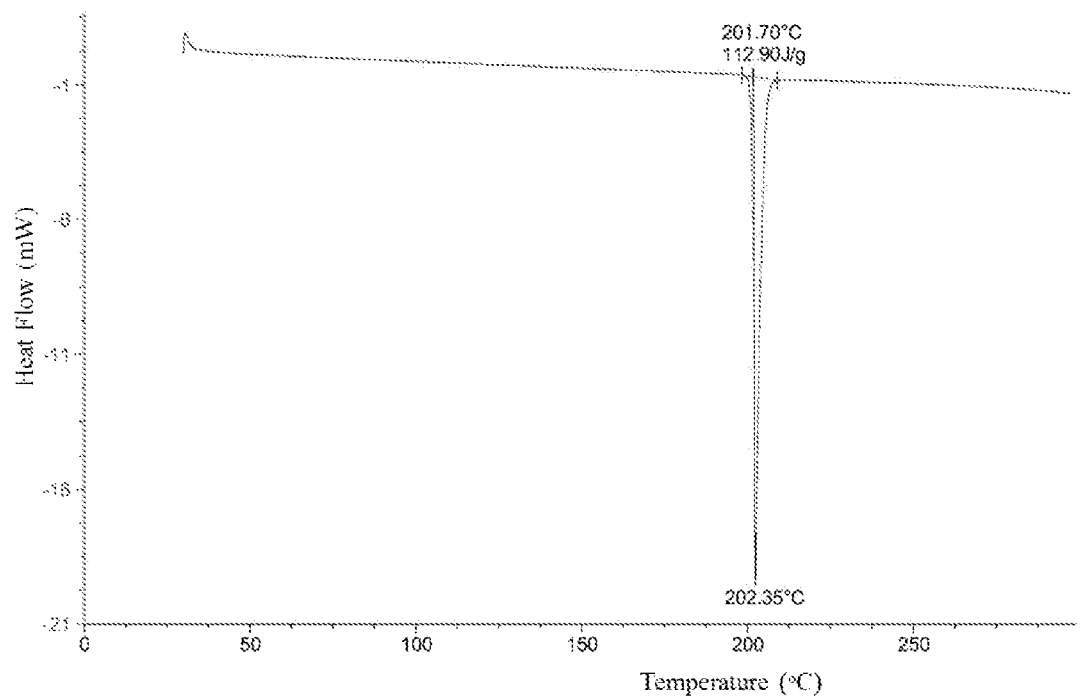
FIG. 2 shows the DSC pattern of the Crystal Form A of Compound 1.

5. The Crystal Form A of Compound 1 according to claim 4, wherein the Crystal Form A has a DSC pattern as shown in FIG. 2.

6. The Crystal Form A of Compound 1 according to claim 1, wherein the Crystal Form A has a thermogravimetric analysis curve, wherein the weight loss at 100.00±2° C. is 0.02039%.

Figure 3:
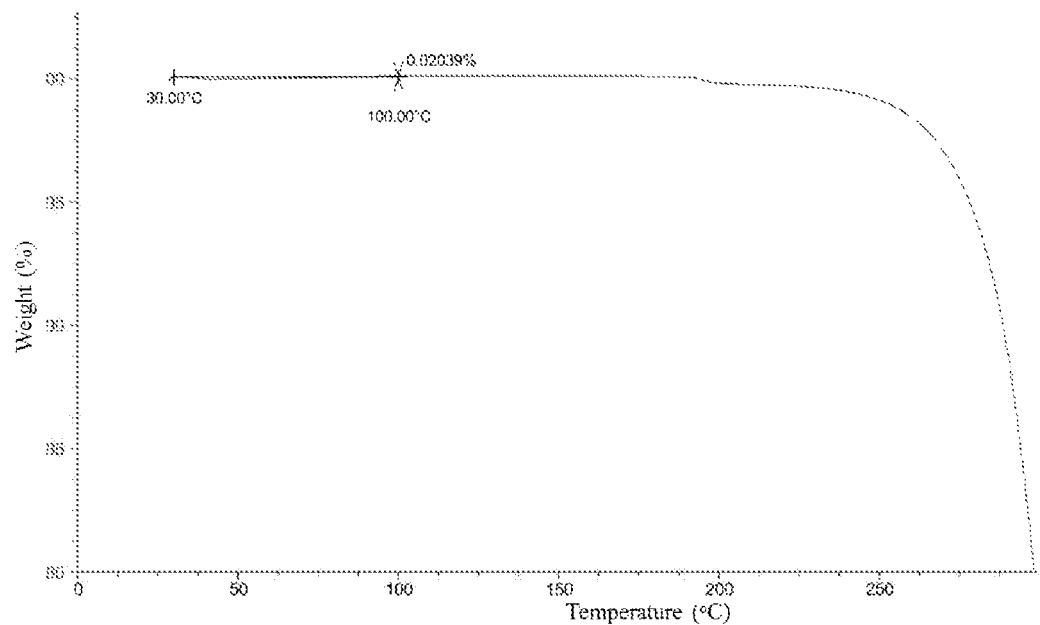
FIG. 3 shows the TGA pattern of the Crystal Form A of Compound 1.

7. The Crystal Form A of Compound 1 according to claim 6, wherein the Crystal Form A has a TGA pattern as shown in FIG. 3.

8. A process for preparing the Crystal Form A of Compound 1, according to claim 1, comprising
adding Compound 1 into an alcohol solvent, a ketone solvent, an ether solvent, a mixed solvent of alcohol solvent and water, a mixed solvent of ketone solvent and water or a mixed solvent of ether solvent and water;
heating for dissolution, and then cooling for crystallization to obtain the Crystal Form A.

9. The process for preparing the Crystal Form A of Compound 1 according to claim 8, wherein
the alcohol solvent is selected from the group consisting of methanol, ethanol and isopropanol.

10. The process for preparing the Crystal Form A of Compound 1 according to claim 8, wherein
the ketone solvent is selected from the group consisting of acetone and butanone.

11. The process for preparing the Crystal Form A of Compound 1 according to claim 8, wherein
the ether solvent is selected from the group consisting of glycol dimethyl ether.

12. The process for preparing the Crystal Form A of Compound 1 according to claim 8, wherein
the mixed solvent of alcohol solvent and water is selected from the group consisting of a mixed solvent of ethanol and water.

13. The process for preparing the Crystal Form A of Compound 1 according to claim 12, wherein
in the mixed solvent of alcohol solvent and water, the volume ratio of alcohol solvent to water is selected from the group consisting of 1:0.2-1.5.

14. A method for treating a disease associated with PDE4 receptor in a subject in need thereof, comprising administering to the subject a therapeutically effective amount of the Crystal Form A of Compound 1 according to claim 1, wherein the disease associated with PDE4 receptor is selected from the group consisting of psoriasis, psoriatic arthritis, chronic obstructive pneumonia, ankylosing spondylitis, and inflammatory bowel disease.

* * * * *